United States Patent

Berliner et al.

[11] Patent Number: 5,849,327
[45] Date of Patent: Dec. 15, 1998

[54] DELIVERY OF DRUGS TO THE LOWER GASTROINTESTINAL TRACT

[75] Inventors: David L. Berliner, Atherton; Sergio Nacht, Redwood City, both of Calif.

[73] Assignee: Advanced Polymer Systems, Inc., Redwood City, Calif.

[21] Appl. No.: 720,335

[22] Filed: Sep. 27, 1996

Related U.S. Application Data

[63] Continuation-in-part of Ser. No. 432,619, May 2, 1995, abandoned, which is a continuation-in-part of Ser. No. 282,836, Jul. 29, 1994, abandoned.

[51] Int. Cl.$^6$ .............................. A61K 9/26; A61K 9/30; A61K 9/48; A61K 9/52
[52] U.S. Cl. ..................... 424/463; 424/451; 424/456; 424/463; 424/464; 424/469; 424/474; 424/475; 424/479; 424/482
[58] Field of Search ..................... 424/451, 456, 424/458, 461, 463, 486, 489, 499, 464, 469, 474–482

[56] References Cited

U.S. PATENT DOCUMENTS

| | | | |
|---|---|---|---|
| 3,946,110 | 3/1976 | Hill | 424/230 |
| 4,198,395 | 4/1980 | DeSimone | 424/79 |
| 4,198,396 | 4/1980 | Seidel et al. | 424/81 |
| 4,221,871 | 9/1980 | Meitzner et al. | 521/29 |
| 4,575,539 | 3/1986 | DeCrosta et al. | 525/283 |
| 4,690,825 | 9/1987 | Won | 424/501 |
| 4,806,360 | 2/1989 | Leong et al. | 424/487 |
| 4,904,474 | 2/1990 | Theeuwes et al. | 424/468 |
| 5,145,675 | 9/1992 | Won | 424/78.31 |
| 5,178,866 | 1/1993 | Wright et al. | 424/473 |
| 5,316,774 | 5/1994 | Eury | 424/501 |
| 5,422,121 | 6/1995 | Lehmann et al. | 424/464 |
| 5,443,841 | 8/1995 | Milstein et al. | 424/451 |
| 5,505,966 | 4/1996 | Edman et al. | 424/493 |
| 5,525,634 | 6/1996 | Sintov et al. | 514/777 |

FOREIGN PATENT DOCUMENTS

| | | |
|---|---|---|
| 322392 A1 | 6/1989 | European Pat. Off. . |
| 466566 A2 | 1/1992 | European Pat. Off. . |
| 485840 A2 | 5/1992 | European Pat. Off. . |
| 3234331 A1 | 3/1984 | Germany . |
| 291668 A | 2/1986 | Germany . |
| 91/16881 | 11/1991 | WIPO . |
| WO 91/16881 A | 11/1991 | WIPO . |
| WO 91/19483 A1 | 12/1991 | WIPO . |
| 92/00732 | 1/1992 | WIPO . |
| WO 92/00732 | 1/1992 | WIPO . |
| WO 97/27843 A2 | 8/1997 | WIPO . |

OTHER PUBLICATIONS

Ashford et al., "An Evaluation of Pectin as a Carrier for Drug Targeting to the Colon", *Journal of Controlled Release*, 26, 213–220 (1993).

Rubenstein et al., "In Vitro Method for Drug Release Analysis from Microbially Controlled Delivery Systems", *Proceed. Intern. Symp. Control. Rel. Bioact. Mater.*, 17, 466–467 (1990).

Rubenstein et al., "Pectic Salt as a Colonic Delivery System", *Proceed. Intern. Symp. Control. Rel. Bioact. Mater.*, 18, 221–222 (1991).

(List continued on next page.)

*Primary Examiner*—Gollamudi S. Kishore
*Attorney, Agent, or Firm*—Heller Ehrman White & McAuliffe

[57] ABSTRACT

Diseases of the colon are treated by oral ingestion of a unit dosage form containing a plurality of porous microscopic beads, the pores containing an active agent or drug and plugged with a polysaccharide that is chemically degradable by colon-specific bacteria. The dosage form further contains a coating of an enteric material that remains intact until the dosage form reaches the colon.

34 Claims, 1 Drawing Sheet

OTHER PUBLICATIONS

Salyers et al., "Fermentation of Mucins and Plant Polysaccharides by Anaerobic Bacteria from the Human Colon", *Applied and Environmental Microbiology*, 34, 529–533 (1977).

Salyers et al., "Carbohydrate Metabolism in the Human Colon", *Human Intestinal Microflora in Health and Disease*, Chapter 6, 129–146 (1983).

Vercellotti, et al., "Breakdown of Mucin and Plant Polysaccharides in the Human Colon", *Can. J. Biochem.*, 55, 1190–1196 (1977).

Wilson, "The Gastrointestinal Microflora", *Textbook of Gastroenterology*: Carbohydrate Metabolism, 1, 532–543 (1991).

Cui et al., "A Budesonide Prodrug Accelerates Treatment of Colitis in Rats", *Gut*, 35, 1439–1446 (1994).

Geary et al., "Vancomycin and Insulin Used as Models for Oral Delivery of Peptides", *Journal of Controlled Release*, 23, 65–74,(1993).

Haeberlin et al., "In Vitro Evaluation of Dexamethasone-β-D-Glucuronide for Colon-Specific Drug Delivery", *Pharm. Res.*, 10, 1553–1562 (1993).

Levine, et al. "Coating of Oral Beclomethasone Dipropionate Capsules With Cellulose Acetate Phthalate Enhances Delivery of Topically Active Antiinflammatory Drug to the Terminal Ileum", *Gastroenterology* 92, 1037–1044, (1987).

McLeod et al., "A Glucocorticoid Prodrug Facilitates Normal Mucosal Function in Rat Colitis Without Adrenal Suppression", *Gastroenterology*, 106, 405–413 (1994).

Milojevic et al., "Amylose as a Coating for Drug Delivery to the Colon: Preparation and in Vitro Evaluation Using 5–Aminosalicylic Acid Pellets", *Journal of Controlled Release*, 38, 75–84 (1996).

Rutgeerts et al., "A Comparison of Budenoside with Prednisolone for Active Crohn's Disease", *New England Journal of Medicine*, 331, 842–845 (1994).

Saffron, et al. "A New Approach to the Oral Administration of Insulin and Other Peptide Drugs", *Science*, 233, 1081–1084 (1986).

Theeuwes, F. "Elementary Osmotic Pump", *Journal of Pharmaceutical Sciences*, 64, 1987–1991 (1975).

5,849,327

DELIVERY OF DRUGS TO THE LOWER GASTROINTESTINAL TRACT

CROSS REFERENCE TO RELATED APPLICATIONS

This application is a continuation-in-part of U.S. Pat. application Ser. No. 08/432,619, filed May 2, 1995, now abandoned, which was a continuation-in-part of application Ser. No. 08/282,836, filed Jul. 29, 1994, now abandoned. The contents of both applications 08/432,619 and 08/282,836 are hereby incorporated herein by reference.

BACKGROUND OF THE INVENTION

1. Field of the Invention

This invention relates to the treatment of diseases of the colon, such as inflammatory bowel disease. More particularly, it relates to a dosage form for an active agent and the method of its use in topically treating disease in the colon.

2. Description of the Prior Art

Many conditions either originate or are expressed in the lumen of the gastrointestinal (G.I.) tract or in the tissue intermediate to the lumen. Inflammatory bowel diseases, such as ulcerative colitis and Crohn's disease, are examples of such conditions. Current therapies for inflammatory bowel diseases involve systemic administration of a formulation containing an active drug. Unfortunately, the drug is absorbed systemically even though the site where the drug is needed is a localized area in the bowel. Thus, to achieve a therapeutically effective local concentration at the site of the disease, one must administer enough of the formulation that the systemic concentration is relatively high. The disadvantage is that high systemic concentrations can have damaging side effects. An example is the administration of prednisolone for inflammatory bowel disease. Although administered for purposes of localized action, this steroid is absorbed systemically, and prolonged exposure from continued systemic absorption can result in atrophy of adrenal glands. Steroids have also been administered by enema, but this does not prevent systemic absorption.

One method of preventing systemic absorption is the use of prodrug techniques. The prodrug is one that is not absorbed until it reaches a particular region of the G.I. tract where it is transformed to an absorbable form and thereby becomes active. An example is sulphasalazine which is used in the treatment of inflammatory bowel disease.

While the prodrug approach has worked for some drugs it is limited in scope due to its dependence upon the chemistry of the prodrug and the drug, and how the former is transformed to the latter in the G.I. environment. This approach requires the development of a new prodrug for each active species, and as new chemical entities, prodrugs require independent regulatory approval.

SUMMARY OF THE INVENTION

The disadvantages noted above are addressed by the present invention, which resides in a composition and method for the treatment of diseases of the colon by oral ingestion of a drug specially formulated to pass intact through the stomach and to be released at a controlled rate for therapeutic action upon reaching the colon. These effects are achieved in a manner independent of the chemistry of the drug or of any relationship between the drug itself and the environment of the G.I. tract. The formulation comprises microscopic beads with pores containing the drug, the pores being plugged with a polysaccharide that is chemically degradable only by bacterial enzymes that are present in the colon, the beads being assembled into a unit dosage form suitable for oral administration yet coated with an enteric coating that protects that dosage form from the stomach environment and allows it to pass intact through the stomach and into the colon. The dosage form thus remains intact until it reaches the small intestine or regions close thereto, where the enteric coating degrades and exposes the polysaccharide that plugs the pores. While some dissolving of the polysaccharide occurs upon exposure in this manner, chemical degradation of the polysaccharide occurs only in the large intestine (i.e., the colon). Once the polysaccharide is degraded sufficiently to expose the active agent in the pores, the beads release the active agent at a rate which is slow and controlled due to the pore structure.

The microscopic beads are rigid polymeric beads that remain rigid and insoluble throughout their travel through the G.I. tract, each microscopic bead containing a substantially noncollapsible internal pore network accessible through openings on the surfaces of the beads. The polymer from which the beads are formed can be linear or crosslinked. The active agent retained in the pore network of the beads is any of a wide variety of therapeutic drugs, examples of which are corticosteroids and non-steroidal anti-inflammatory agents for treatment of inflammatory bowel disease, anti-tumor agents for treatment of colonic malignancies, anti-parasitic agents for treatment of parasites, antibiotics for treatment of infections, laxatives for treatment of constipation, and drugs such as bismuth subsalicylate, trimethoprim-sulfamethoxazole, and doxycycline and various other antibiotics for treatment of diarrhea.

The microscopic beads used in the present invention have previously been used as a delivery system for external topical skin administration of active agents. When topically administered, the beads were shown to be capable of releasing the active agents at a controlled rate. It has now been found that these microscopic beads when formulated with the polysaccharides and enteric coatings described above constitute a delivery system that can be administered orally for the safe and efficacious treatment of diseases of the colon without harm to, or substantial release of the active agent at, other locations along the G.I. tract. The inherently slow release rate of active agents from the pores of the microscopic beads is thus now further combined with localization of the release. In certain cases a small degree of systemic absorption of the active agents may occur, but side effects are substantially absent since the rate of systemic absorption is at most very slow due to the combination of drug, microbeads, pore structure, and polysaccharide in the formulation.

This method of administering the active agent is thus a topical administration since the active agent is not released from the dosage form until it reaches the site of interest. The agent thus contacts the site of interest directly through the wall of the colon, rather than being delivered to the colon through the blood stream which would carry the agent active to other (not diseased) parts of the body as well. The use of porous microbeads for a controlled and sustained release rate maximizes this topical effect and minimizes systemic effects.

In preferred embodiments, the dosage form is a pharmaceutical capsule (such as a gelatin capsule) or tablet containing a multitude of microscopic beads with the selected active agent in the porous network of the individual beads, the polysaccharide on the surfaces of the individual beads and plugging the pores, and an enteric coating surrounding the capsule or tablet. The active agent can be present in the capsule or tablet in varying amounts not critical to this invention, although in most cases the amount per capsule or tablet will generally be in the range of about 0.1–100 mg, with additional acceptable ranges about 1–100 mg, about 3–20 mg, and about 5–20 mg.

Examples of microscopic beads are those formed from styrene-divinylbenzene copolmyer, methyl methacrylate-ethylene glycol dimethacrylate copolymer, poly(methyl acrylate), poly(methyl methacrylate), and polystyrene, and analogs thereof. Typical bead diameters are about 5–200 microns, preferably about 10–40 microns.

Two of the many conditions that can be successfully treated by the composition and method of this invention are ulcerative colitis, which affects only the large intestine (a portion or its entire length), and Crohn's disease, which affects both the terminal ileum and the ascending colon. A dosage form for ulcerative colitis according to the present invention is formulated so that it will initially remain intact in the G.I. tract and degrade only in or near the large intestine. For Crohn's disease the dosage form is formulated to initially remain intact in the G.I. tract until reaching the junction of the ileum with the colon where it will degrade and release the active agent.

BRIEF DESCRIPTION OF THE DRAWINGS

FIG. 3b is an enlarged cross section of one of the particles contained in the interior of the capsule of FIG. 3a.

DETAILED DESCRIPTION OF THE INVENTION AND PREFERRED EMBODIMENTS

Microscopic Beads

Figure 1:
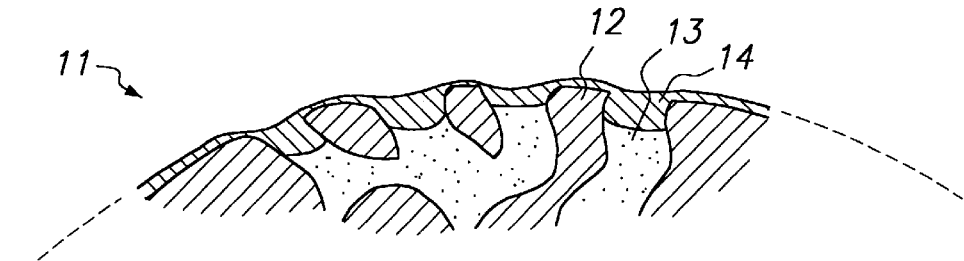
FIG. 1 is a cross section of a porous microscopic bead impregnated with an pharmacological agent in the pores, and the pores plugged with a polysaccharide for use in the formulations of this invention. The view shown in the Figure is that of a region close to the surface of the bead.

Microscopic beads that can be used in connection with the present invention are known in the art and are described in detail in Won, U.S. Pat. No. 5,145,675, entitled "Two Step Method for Preparation of Controlled Release Formulations," issued Sep. 8, 1992, assigned to Advanced Polymer Systems, Inc. The disclosure of U.S. Pat. No. 5,145,675 is incorporated herein by reference. One particular type of microscopic bead contemplated for use in this invention are co-polymers of styrene and divinylbenzene, whose preparation is disclosed in Example 1.1 of U.S. Pat. No. 5,145,675. The same example also illustrates a method for entrapping steroids within the porous network of the polymeric beads. Another type of microscopic bead contemplated for use herein are copolymers of methyl methacrylate and ethylene glycol dimethacrylate. The preparation of microscopic beads of this composition is described in Example 6.2 of U.S. Pat. No. 5,145,675. In general, the diameter of an individual bead is not critical and may vary. In most cases, however, the most convenient diameter is from about 5 microns to about 200 microns. Particles of the aforementioned types are commercially available from Advanced Polymer Systems, Inc., of Redwood City, Calif., in the form of empty particles or as particles which have been loaded with the active agents utilized in the present invention.

Pore-plugging Polysaccharide Degradable by Colonic Bacteria

As noted, one of the elements responsible for restricting release of the drug from the dosage form to locations in or near the colon is the polysaccharide that plugs the pore openings and seals the active agent inside the pores. The polysaccharide is one that is chemically degradable only by the action of bacteria that are specific to and generally confined in the colon. The degradation of the coating by these bacteria result in the removal of the polysaccharide from the pore openings and consequently the release of the drug. Examples of polysaccharides that meet this description are pectin, arabinogalactose, chitosan, chondroitin sulfate, cyclodextrin, dextran, galactomannan (guar gum), and xylan. A preferred polysaccharide is pectin.

The amount of colon-degradable polysaccharide present in the formulation can vary and is not critical, although amounts considered optimal will depend on the particular polysaccharide selected. The amount in any event will be sufficient to plug the pore openings. For pectin, it has been shown that dissolution and release will depend on the particular pectin composition, primarily its methoxy content. Thus, pectins with a high degree of methoxylation demonstrate a higher degree of protection for the dosage form than those pectins with a lower degree of methoxylation. Pectin USP with a degree of methoxylation of 70% is an example of a preferred material which can be obtained from Bulmer Pectin, UK.

Enteric Coating

Examples of enteric coating materials that are gastro resistant and yet degrade in the intestines are disclosed in Eury et al., U.S. Pat. No. 5,316,774, entitled "Blocked Polymeric Particles Having Internal Pore Networks for Delivering Active Substances to Selected Environments," issued May 31, 1994, the contents of which are hereby incorporated herein by reference. Other examples are known to those skilled in the art.

One class of enteric coating materials of the above description are those that remain intact in the environment of the stomach but solubilize at the higher pH of the intestines. Materials of this type are known in the art for use as coatings for solid core drug formulations. The most effective enteric materials are polyacids having a $pK_a$ of from about 3 to 5. Preferred are those whose carboxylic acid groups are transformed to carboxylate groups at a pH of from about 5 to 7. These copolymers are resistant to gastric juices. Exemplary materials include fat-fatty acid mixtures, cellulose acetate phthalates, copolymers of methacrylic acid and methyl methacrylate, copolymers of methacrylic acid and ethylacrylate, and polymers or copolymers in general containing acrylic acid or alkyl-substituted acrylic acids as monomers. The polymers, and particularly those containing acrylic acid or an alkyl-substituted acrylic acid can be applied to the outer surface of the dosage form either by in situ polymerization or by deposition from an aqueous dispersion. Examples of copolymers useful as enteric coating materials are listed in Table I.

TABLE I

| Copolymer | Molecular Weight | Preferred Monomer Ratio |
| --- | --- | --- |
| poly(methacrylic acid, ethylacrylate) | 250 kD | 1:1 |
| poly(methacrylic acid, methylmethacrylate) | 135 kD | 1:2 |

The coating thickness may vary and is not critical to this invention. In most applications and with most coating materials, best results are obtained with coatings of thickness in the range of from about 0.1 mm to about 1.0 mm.

Additional Features

The term "unit dosage form" as used herein denotes a formulation configured as a self-contained dosage containing sufficient active agent to constitute the dosage for a single administration, when taken either as the sole treatment or as one of a series of periodic administrations. The present invention contemplates any suitable dosage form that can be used for oral drug delivery. In this regard the polymeric particles carrying the drug may be incorporated into a variety of known dosage forms, as described in, for example, Remington's Pharmaceutical Sciences, Mack Publishing Company, Easton Pa., 16th Ed., 1982, the disclosure of which is incorporated herein by reference. The unit dosage form will contain a preselected quantity of active agent(s) contained within the porous microscopic beads. Pharmaceutically acceptable non-toxic dosage forms are prepared using conventional excipients, such as pharmaceutical grades of mannitol, lactose, starch, magnesium stearate, sodium saccharin, talcum, cellulose, glucose, sucrose, magnesium, carbonate, and the like. Such compositions may be in the form of solutions, suspensions, tablets, pills, capsules, powders, and the like.

As noted above, the invention finds utility in the treatment of diseases of the colon. One type of disease to which the dosage form and method of this invention are particularly well suited is inflammatory bowel disease. Examples of drugs to be utilized for treatment of inflammatory bowel disease are hydrocortisone, beclomethasone dipropionate, tixocortol pivalate, budesonide, dexamethasone, prednisone, prednisolone and triamcinolone acetonide. Non-steroidal anti-inflammatory agents such as amino salicylate and sulfasalazine are also contemplated. Recent clinical studies have shown that ulcerative colitis can also be treated with cyclosporine, a drug usually given to transplant patients, and this is contemplated for use herein as well. Prodrugs are another class of drugs contemplated for use herein, where they are placed in the pores of the microscopic beads in the same manner as the active drugs described above. Examples of prodrugs are dexamethasone-succinate-dextran (*Gastroenterology*, 1994, 106:2 405–413), budesonide-β-glucuronide (*Gut*, 1994, 35: 1439–1446), and dexamethasone-β-D-glucuronide (*Pharm. Res.*, 1993, 10: 1553 . 1562).

In compositions for the treatment of colonic malignancies, any suitable anti-tumor agent known in the art for the treatment of localized malignancies can be incorporated in the dosage form. Examples of anti-tumor agents suitable for use in this invention are methotrexate, 5-fluorouracil, and similarly functioning anti-neoplastic agents, such as tamoxifen, cyclophosphamide, mercaptopurine etoposide, indomethacin, semustine, fluorouracil, floxuridine and mitomycin. For the treatment of infections of the colon, antibiotics (including antibacterials) which are suitable for use in this invention include sulphanilamides and their derivatives, and other antibiotics specifically designed to treat particular bacterial infections associated with food ingestion. Additional examples include sulfonamides, norfloxacin, chloramphenicol, tetracyclines and vancomycin.

For treatment of parasites, suitable anti-parasitic agents can be used, such as diloxanide furoate, metronidazole, quinacrine, tetracyclines, iodoquinol, dehydroemetine, amphotericin B, mebendazole and thiabendazole.

Figure 2:
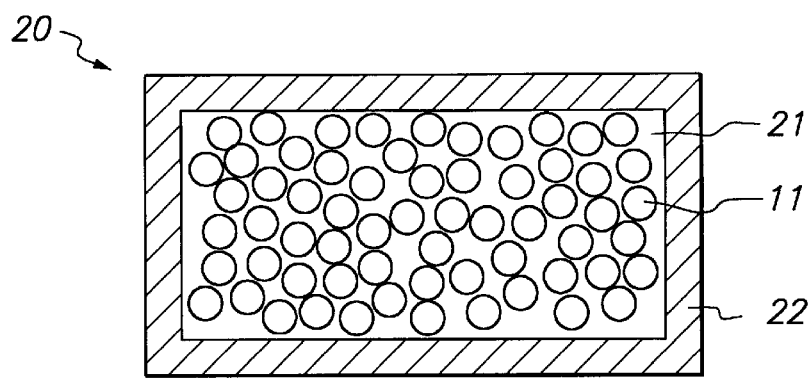
FIG. 2 is a cross section of a tablet embodying a unit dosage form within the scope of this invention.

For a further understanding of the invention, reference is made to FIGS. 1, 2 and 3.

A cross section of a region close to the surface of an impregnated microscopic bead 11 for use in the composition and method of this invention is shown in FIG. 1. The bead itself is a polymeric matrix 12 with an internal network of pores. Residing in the pores is an active pharmacological agent 13, and the pore openings are plugged with the polysaccharide 14 that is degradable by colon-specific enzymes.

A multitude of impregnated microscopic beads such as those shown in FIG. 1 are shown in FIG. 2, where the beads are combined into a compressed tablet 20, shown in cross section. The individual beads 11 occupy the interior of the tablet, and the polysaccharide 21 that is degradable by colon-specific enzymes not only coats the beads and plugs their pore openings, but also fills the volume in between the beads. The exterior of the tablet is the enteric coating material 22, coating the tablet.

Figure 3A:
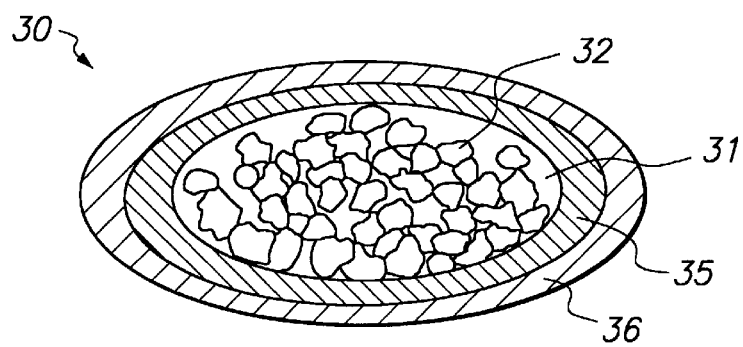
FIG. 3a is a cross section of a capsule embodying a unit dosage form within the scope of this invention.
Figure 3B:
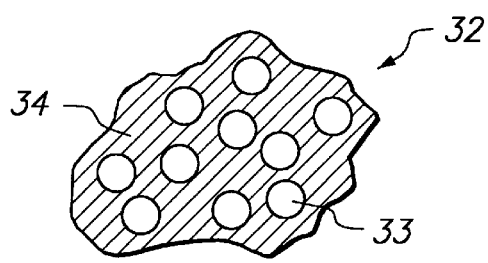

A cross section of a capsule 30 is shown in FIG. 3*a*, representing a second dosage form as an alternative to the tablet 20 of FIG. 2. The capsule is hollow, with its void space 31 filled with a multitude of loose particles 32, one of which is shown in enlarged cross section in FIG. 3*b*. The particles are formed by dispersing drug-impregnated microbeads such as those represented by FIG. 1 (minus the polysaccharide coating) in liquid polysaccharide, solidifying the polysaccharide, and granulating the solidified mass into particles. Each particle 32 thus consists of a multitude of drug-impregnated microbeads 33 dispersed through a matrix of solid polysaccharide 34, i.e., the same polysaccharide that is used in the tablet of FIGS. 1 and 2. The capsule 35 is gelatin, coated with the enteric material 36.

The following examples are offered for purposes of illustration only.

EXAMPLE 1

Tablets containing a suitable amount of a corticosteroid entrapped in a MICROSPONGE® (registered trademark of Advanced Polymer Systems, Inc. of Redwood City, Calif., applied to its polymeric microbeads having an internal porous network) system are prepared with the following general formulation:

| Tablet Component | Weight |
| --- | --- |
| MICROSPONGE ® System with corticosteroid | 250 mg |
| Pectin | 200 mg |
| Dibasic Calcium Phosphate | 100 mg |
| EUDRAGIT 100S | 100 mg |
| Magnesium Stearate | 10 mg |

EUDRAGIT 100S is a poly(methylnethacrylate-co-methacrylic acid) blocking agent for enteric coating from Rohm Pharma GmbH, Darmstadt, West Germany.

| A) Hydrocortisone 10% in Acrylates Copolymer | |
| --- | --- |
| (Formula per gram of entrapment) | |
| Hydrocortisone | 100 mg |
| Acrylates Copolymer (APS Type E 101) | 900 mg |

APS Type E 101, E 140, and E 104 are polymer beads formed from a copolymer of methl methacrylate-ethylene glycol dimethacrylate, available from Advanced Polymer Systems, Inc., Redwood City, Calif. The polymers differ by particle size and porosity and all are within the range of about 8 to 25 microns in diameter.

This entrapment is prepared as described in U.S. Pat. No. 5,145,675. Namely, a 5% w/w hydrocortisone solution is prepared by adding 600 mg of hydrocortisone to 12 g of ethanol and then heated to 65° C. Small volumes of this solution (less than 1 mL) are then added to 4.5 g of blank polymer Type E 101 in an amber bottle and then slowly stirred using a spatula for several seconds. This is repeated until a total of 5 g of solution has been added. The bottle is capped and then placed on a roller mill for one hour to mix the contents. The polymer is then dried in an oven at 65° C. for 2.5 hours. Due to the low solubility of hydrocortisone in the organic solvents used to prepare the entrapment, to achieve adequate levels of drug in the polymer to make it suitable for therapy, this process is repeated for a second entrapment step with drying of entrapped polymer in the oven at 50° C. overnight.

B) Beclomethasone 5% in Acrylates Copolymer (Formula per gram of entrapment)

| | |
|---|---|
| Beclomethasone Dipropionate | 50 mg |
| Acrylates Copolymer (APS Type E 140) | 950 mg |

A 2.5% w/w beclomethasone solution is prepared by adding 300 mg of beclomethasone to 12 g of ethanol and then heated to 65° C. Small volumes of this solution (less than 1 mL) are then added to 4.75 g of blank polymer in an amber bottle and then slowly stirred using a spatula for several seconds. This is repeated until a total of 5 g of solution has been added. The bottle is capped and then placed on a roller mill for one hour to mix the contents. The polymer is then dried in an oven at 65° C. for 2.5 hours. This process is repeated for the second entrapment step with drying of entrapped microsphere polymer in the oven at 50° C. overnight.

C) Budesonide 5% in Acrylates Copolymer (Formula per gram of entrapment)

| | |
|---|---|
| Budesonide | 50 mg |
| Acrylates Copolymer (APS Type E 104) | 950 mg |

A 2.5% w/w budesonide solution is prepared by adding 300 mg of budesonide to 12 g of tetrahydrofuran and then heated to 65° C. Small volumes of this solution (less than 1 mL) are then added to 4.75 g of blank polymer in an amber bottle and then slowly stirred using a spatula for several seconds. This is repeated until a total of 5 g of solution has been added. The bottle is capped and then placed on a roller mill for one hour to mix the contents. The polymer is then dried in an oven at 65° C. overnight. This process is repeated for a second entrapment to obtain the desired payload.

Tablets are prepared by mixing the indicated amount of polymer entrapment containing the drug and the other ingredients listed in the formulation, except the Eudragit. Tablets are produced by compression compaction using a stainless steel mold and a suitable hydraulic press.

These tablets are then pan-coated with the Eudragit 100S to provide an enteric coating that will allow the tablets to traverse through the stomach without disintegration or premature release of the drug. To coat the tablets, they are placed in a suitably heated rotating drum at about 40°–45° C. and, while rotating, an appropriate amount of an Eudragit solution in ethanol, isopropanol or acetone is slowly added to the tumbling tablets to obtain a uniform coating by evaporation of the solvent.

(Formula per Capsule)

| | |
|---|---|
| MICROSPONGE ® System with corticosteroid | 250 mg |
| Pectin (or other suitable polysaccharide) | 150 mg |

Polymer containing the entrapped corticosteroid is prepared as described in Example 1 A), B) or C) above.

A pectin solution is prepared by dissolving 1.5 g of pectin (moistened with 0.5 mL of ethanol to facilitate dissolution) in 30 ml of water heated to about 50° C. The suspension is maintained at this temperature with gentle stirring until a clear viscous solution is obtained.

Then, 2.5 g of microspheres containing the corticosteroid is placed in a suitable glass or metal container such that it can be rotated while heated and its contents stirred to prevent agglomeration. The pectin solution is then added slowly and in small portions to the polymer, while rotating the vessel and continue heating. As the mixture dries, more pectin solution is added until completion. A granular material, with granules about 0.6–1.0 mm in diameter is obtained. Larger clumps are easily broken into smaller particles with a glass rod or other suitable utensil.

The dry material thus obtained is divided into 400 mg portions and each portion is placed into a gelatin capsule. Alternatively, if smaller capsules are desired, 200 mg portions can be used.

These capsules, properly sealed, are then placed in a mildly heated coating pan (about 40° C.) and, while rotating, an EUDRAGIT 100S solution in ethanol, isopropanol or acetone is slowly added to the tumbling capsules to obtain a uniform coating when the solvent evaporates.

Similar examples of tablet or capsule configurations can be designed by using polymeric entrapments of other drugs like anti-tumor agents, antibacterials, etc., in MICROSPONGE® Systems of different polymer compositions, particle size, and porosities as described in U.S. Pat. No. 5,145,675.

The following examples illustrate the safety of the dosage form and method.

EXAMPLE 3

This example is a study involving the gastrointestinal tract in subjects with ileostomy. The subjects were all given a capsule similar to that described in Example 2 wherein the porous microscopic beads were loaded with $^{14}$C-hydrocortisone.

In this study, $^{14}$C-hydrocortisone was measured in both the urine and ileal effluent for 3–5 days after ingestion of a capsule containing the test material. In three of the subjects, the urine and ileal effluents were collected frequently so that the elimination of $^{14}$C could be timed. The ileal effluents from one subject were accidentally destroyed during the drying process. Thus, only the data from four subjects can be evaluated.

Tables II and III list the percentages of $^{14}$C recovered in the ileal effluent and urine for each of the four subjects whose ileal effluent was not destroyed. Table III shows recovery for the entire collection, while Table IV shows the timing of the excretion in ileal effluent or urine.

TABLE II

Recovery of $^{14}$C-Hydrocortisone in Entire Collection

| Subject | Percent Recovered | |
| --- | --- | --- |
| | Ileal Effluent | Urine |
| 1 | 53.8 | 46.2 |
| 2 | 98.0 | 2.0 |
| 3 | (unable to evaluate) | |
| 4 | 93.3 | 6.7 |
| 5 | 96.3 | 6.7 |
| Mean | 85.4 | 14.6 |

TABLE III

Recovery on Timed Basis

Percent Recovered by Time Interval

| | Ileal Effluent | | Urine | |
| --- | --- | --- | --- | --- |
| Subject | Hours | Percent | Hours | Percent |
| 1 | 0–24 | 49.3 | 0–24 | 35.0 |
| | 24–48 | 4.3 | 24–48 | 10.9 |
| | 48–72 | 0.3 | 48–72 | 0.4 |
| | 0–14 | 0.0 | 0–22 | 0.1 |
| | 14–22 | 4.3 | 22–24 | 0.5 |
| | 22–25 | 85.8 | 24–29 | 0.9 |
| | 25–31 | 0.8 | 29–32 | 0.2 |
| | 31–38 | 3.4 | 32–36 | 0.1 |
| | 38–120 | 0.0 | 36–120 | 0.0 |
| 3 | (unable to evaluate) | | | |
| 4 | 0–3 | 0.0 | 0–3 | 0.1 |
| | 3–9 | 20.5 | 3–9 | 3.1 |
| | 9–16 | 71.5 | 9–16 | 2.4 |
| | 16–25 | 1.2 | 16–25 | 0.9 |
| | 25–96 | 0.0 | 25–32 | 0.2 |
| | | | 32–96 | 0.0 |
| 5 | 0–5 | 0.5 | 0–6 | 0.0 |
| | 5–16 | 93.5 | 6–10 | 0.3 |
| | | | 10–12 | 0.8 |
| | | | 12–22 | 1.4 |
| | 16–24 | 0.7 | 22–24 | 0.6 |
| | 24–28 | 0.3 | 24–30 | 0.2 |
| | 28–34 | 0.2 | 30–96 | 0.0 |
| | 34–48 | 0.3 | | |
| | 48–72 | 0.6 | | |
| | 72–96 | 0.3 | | |

An examination of the entire collection results in Table II indicates that in three of the subjects the $^{14}$C excretion was almost entirely in the ileal effluent. In one subject 53.8% of the $^{14}$C was excreted by way of the ileal effluent. The reason for the difference between the results in this one subject compared to the other three is not known.

An examination of the timed excretion data in Table II for the ileal effluents indicates almost all of the excretion occurs within 24 hours after ingestion of the capsule. The exact timing within this 24 hours varied some between the three subjects where such timing could be evaluated. In one, the ileal excretion was greatest at 22–25 hours after ingestion; in another it was at 3–16 hours; and in the third it was 5–16 hours. This variability may be due to differences in residence time for the capsule in the stomach. The transfer of large particles from the stomach to the small intestine depends on many factors. One important factor is the relationship to meals. A capsule such as the one used in this study may not leave the stomach until all nutrients from meals have left the stomach and small intestine.

On the whole, these results indicate that, in a normal individual (no ileostomy), the active ingedient would be released primarily in the colon, thus maximizing the therapeutic benefits of the drug and minimizing systemic absorption.

We claim:

1. A pharmaceutical composition in unit dosage form suitable for oral ingestion for treating diseases of the colon, said composition comprising microscopic polymeric beads insoluble within the GI tract, said beads having pores containing a pharmacologically active agent, said pores having openings plugged with a polysaccharide that is chemically degradable only by bacterial enzymes present in the colon, said beads being assembled in said unit dosage form, said unit dosage form being provided with an enteric coating to allow said unit dosage form to pass intact through the stomach.

2. A pharmaceutical composition in accordance with claim 1 in which said polysaccharide is a member selected from the group consisting of pectin, arabinogalactose, chitosan, chondroitin sulfate, dextran, galactomannan, and xylan.

3. A pharmaceutical composition in accordance with claim 1 in which said polysaccharide is pectin.

4. A pharmaceutical composition in accordance with claim 1 in which said enteric coating is a coating of a member selected from the group consisting of fat-fatty acid mixtures, cellulose acetate phthalates, acrylic acid polymers, acrylic acid copolymers, alkyl-substituted acrylic acid polymers, and alkyl-substituted acrylic acid copolymers.

5. A pharmaceutical composition in accordance with claim 1 in which said enteric coating is a member selected from the group consisting of acrylic acid-containing and methacrylic acid-containing polymers.

6. A pharmaceutical composition in accordance with claim 1 in which said enteric coating is poly(methylmethacrylate-co-methacrylic acid).

7. A pharmaceutical composition in accordance with claim 1 in which said pharmacologically active agent is a member selected from the group consisting of hydrocortisone, beclomethasone dipropionate, tixocortol pivalate, dexamethasone, prednisone, budesonide, prednisolone, and triamcinolone acetonide.

8. A pharmaceutical composition in accordance with claim 1 in which said pharmacologically active agent is an anti-neoplastic agent.

9. A pharmaceutical composition in accordance with claim 1 in which said pharmacologically active agent is an antiparasitic agent.

10. A pharmaceutical composition in accordance with claim 1 in which said pharmacologically active agent is an agent for the treatment of constipation.

11. A pharmaceutical composition in accordance with claim 1 in which said pharmacologically active agent is an agent for the treatment of diarrhea.

12. A pharmaceutical composition in accordance with claim 1 in which said pharmacologically active agent is present in an amount of about 0.1 mg to about 100 mg.

13. A pharmaceutical composition in accordance with claim 1 in which said pharmacologically active agent is present in an amount of about 1 mg to about 100 mg.

14. A pharmaceutical composition in accordance with claim 1 in which said unit dosage form is a tablet.

15. A pharmaceutical composition in accordance with claim 1 in which said unit dosage form is a gelatin capsule.

16. A pharmaceutical composition in accordance with claim 1 in which said microscopic polymeric bead is a copolymer selected from the group consisting of styrene-divinylbenzene and methyl methacrylate-ethylene glycol dimethacrylate.

17. A pharmaceutical composition in accordance with claim 1 in which said microscopic polymeric beads have diameters of about 5 microns to about 200 microns.

18. A method for treating a disease of the colon, the method comprising orally administering to a subject suffering from said disease a pharmaceutical composition in unit dosage form suitable for oral administration comprising microscopic polymeric beads insoluble within the GI tract, said beads having pores containing a pharmacologically active agent, said pores having openings plugged with a polysaccharide that is chemically degradable only by bacterial enzymes present in the colon, said beads being assembled in said unit dosage form, said unit dosage form being provided with an enteric coating to allow said unit dosage form to pass intact through the stomach.

19. A method in accordance with claim 18 in which said polysaccharide is a member selected from the group consisting of pectin, arabinogalactose, chitosan, chondroitin sulfate, dextran, galactomannan, and xylan.

20. A method in accordance with claim 18 in which said polysaccharide is pectin.

21. A method in accordance with claim 18 in which said enteric coating is a coating of a member selected from the group consisting of fat-fatty acid mixtures, cellulose acetate phthalates, acrylic acid polymers, acrylic acid copolymers, alkyl-substituted acrylic acid polymers, and alkyl-substituted acrylic acid copolymers.

22. A method in accordance with claim 18 in which said enteric coating is a member selected from the group consisting of acrylic acid-containing and methacrylic acid-containing polymers.

23. A method in accordance with claim 18 in which said enteric coating is poly(methylmethacrylate-co-methacrylic acid).

24. A method in accordance with claim 18 in which said pharmacologically active agent is a member selected from the group consisting of hydrocortisone, beclomethasone dipropionate, tixocortol pivalate, dexamethasone, prednisone, budesonide, prednisolone, and triamcinolone acetonide.

25. A method in accordance with claim 18 in which said pharmacologically active agent is an anti-neoplastic agent.

26. A method in accordance with claim 18 in which said pharmacologically active agent is an antiparasitic agent.

27. A method in accordance with claim 18 in which said pharmacologically active agent is an agent for the treatment of constipation.

28. A method in accordance with claim 18 in which said pharmacologically active agent is an agent for the treatment of diarrhea.

29. A method in accordance with claim 18 in which said pharmacologically active agent is present in an amount of about 0.1 mg to about 100 mg.

30. A method in accordance with claim 18 in which said pharmacologically active agent is present in an amount of about 1 mg to about 100 mg.

31. A method in accordance with claim 18 in which said unit dosage form is a tablet.

32. A method in accordance with claim 18 in which said unit dosage form is a gelatin capsule.

33. A method in accordance with claim 18 in which said crosslinked polymer is a copolymer selected from the group consisting of styrene-divinylbenzene and methyl methacrylate-ethylene glycol dimethacrylate.

34. A method in accordance with claim 18 in which said microscopic polymeric beads have diameters of about 5 microns to about 200 microns.

* * * * *